(12) United States Patent
Chang et al.

(10) Patent No.: US 12,090,026 B2
(45) Date of Patent: Sep. 17, 2024

(54) THREE-DIMENSIONAL INTRAORAL SCANNER

(71) Applicant: MEDIT CORP., Seoul (KR)

(72) Inventors: Min Ho Chang, Seoul (KR); Soo Bok Lee, Seoul (KR); Ji Woong Chang, Seoul (KR)

(73) Assignee: MEDIT CORP., Seoul (KR)

( * ) Notice: Subject to any disclaimer, the term of this patent is extended or adjusted under 35 U.S.C. 154(b) by 773 days.

(21) Appl. No.: 17/169,294

(22) Filed: Feb. 5, 2021

(65) Prior Publication Data

US 2021/0177555 A1 Jun. 17, 2021

Related U.S. Application Data

(63) Continuation of application No. PCT/KR2019/009871, filed on Aug. 7, 2019.

(30) Foreign Application Priority Data

Aug. 7, 2018 (KR) .................. 10-2018-0091969
Aug. 7, 2019 (KR) .................. 10-2019-0095925

(51) Int. Cl.
*A61C 9/00* (2006.01)
*A61B 1/00* (2006.01)
(Continued)

(52) U.S. Cl.
CPC .......... *A61C 9/006* (2013.01); *A61B 1/00105* (2013.01); *A61B 1/05* (2013.01);
(Continued)

(58) Field of Classification Search
CPC .. H04N 13/254; H04N 13/239; A61C 9/0053; A61C 9/006; A61B 1/00105;
(Continued)

(56) References Cited

U.S. PATENT DOCUMENTS 6,263,234 B1 * 7/2001 Engelhardt .......... A61B 5/0088
250/559.22
2009/0279103 A1 11/2009 Thiel et al.
(Continued)

FOREIGN PATENT DOCUMENTS

KR 10-1043976 B1 6/2011
KR 10-1175616 B1 8/2012
(Continued)

OTHER PUBLICATIONS

Cheol et al "Orthodontic Digital Bracket", Feb. 21, 2018, KR 20180017456 A. (Year: 2018).*
(Continued)

*Primary Examiner* — Sang H Nguyen
(74) *Attorney, Agent, or Firm* — Insight Law Group, PLLC; Seung Lee

(57) ABSTRACT

The present disclosure relates to a three-dimensional intraoral scanner which, in particular, includes: a case which may be drawn in and out of the oral cavity, and has an opening for introducing, into the case, via an end part thereof, the appearance of the oral cavity (hereinafter, image) in the form of light; at least one camera arranged inside the case, and allowing the light introduced via the opening of the case to pass; a light projector which is arranged on one side of the at least one camera and which radiates light into the oral cavity via the opening; an optical element provided to be rotatable while tilting so as to reflect or bend the path of the light from the at least one camera and the light projector from inside the case; and a light path change unit for moving the optical element so as to be adjustable. Therefore, the three-dimensional intraoral scanner may easily obtain image data for the entire oral cavity of a patient.

17 Claims, 17 Drawing Sheets

(51) Int. Cl.
*A61B 1/05* (2006.01)
*A61B 1/07* (2006.01)
*A61B 1/24* (2006.01)
*G02B 7/18* (2021.01)
*G02B 7/182* (2021.01)
*H04N 13/239* (2018.01)
*H04N 13/254* (2018.01)

(52) U.S. Cl.
CPC ............. *A61B 1/07* (2013.01); *A61B 1/24* (2013.01); *G02B 7/1805* (2013.01); *G02B 7/1821* (2013.01); *H04N 13/239* (2018.05); *H04N 13/254* (2018.05)

(58) Field of Classification Search
CPC ............ A61B 1/00193; A61B 1/00006; A61B 1/00172; A61B 1/00183; A61B 1/07; A61B 1/247; A61B 1/24; G01B 11/24; G02B 7/1821; G02B 7/1805
See application file for complete search history.

(56) References Cited

U.S. PATENT DOCUMENTS

| | | | | |
|---|---|---|---|---|
| 2012/0075425 | A1* | 3/2012 | Thiel | A61B 5/0068 348/46 |
| 2012/0092461 | A1* | 4/2012 | Fisker | G01B 11/2513 348/46 |
| 2013/0188012 | A1* | 7/2013 | Bellis | H04N 23/51 348/42 |
| 2013/0286174 | A1* | 10/2013 | Urakabe | A61B 1/04 348/66 |
| 2014/0093835 | A1* | 4/2014 | Levin | A61C 1/088 433/29 |
| 2015/0020325 | A1* | 1/2015 | Yoshida | A46B 5/0095 15/22.1 |
| 2015/0223916 | A1* | 8/2015 | Kim | A61B 5/1079 433/29 |
| 2017/0289523 | A1* | 10/2017 | Lee | H04N 13/207 |

FOREIGN PATENT DOCUMENTS

| | | |
|---|---|---|
| KR | 10-1371211 B1 | 3/2014 |
| KR | 10-1425955 B1 | 8/2014 |
| KR | 10-1844746 B1 | 4/2018 |
| KR | 10-1874547 B1 | 7/2018 |

OTHER PUBLICATIONS

"USB Camera Having Integral Lights", Feb. 5, 2003, KR 200302221 Y1 (Year: 2003).*
Tenu "Optical Imaging Apparatus for Dental Checkup", Oct. 28, 2004, JP2004298503A (Year: 2004).*
International Search Report mailed Nov. 11, 2019 for PCT/KR2019/009871 and its English translation.
Notice of Allowance mailed Aug. 6, 2021 from Korean Intellectual Property Office for Korean Application No. 10-2019-0095925.

* cited by examiner (a)  (b)

(a)

(b)

(a)

(b)

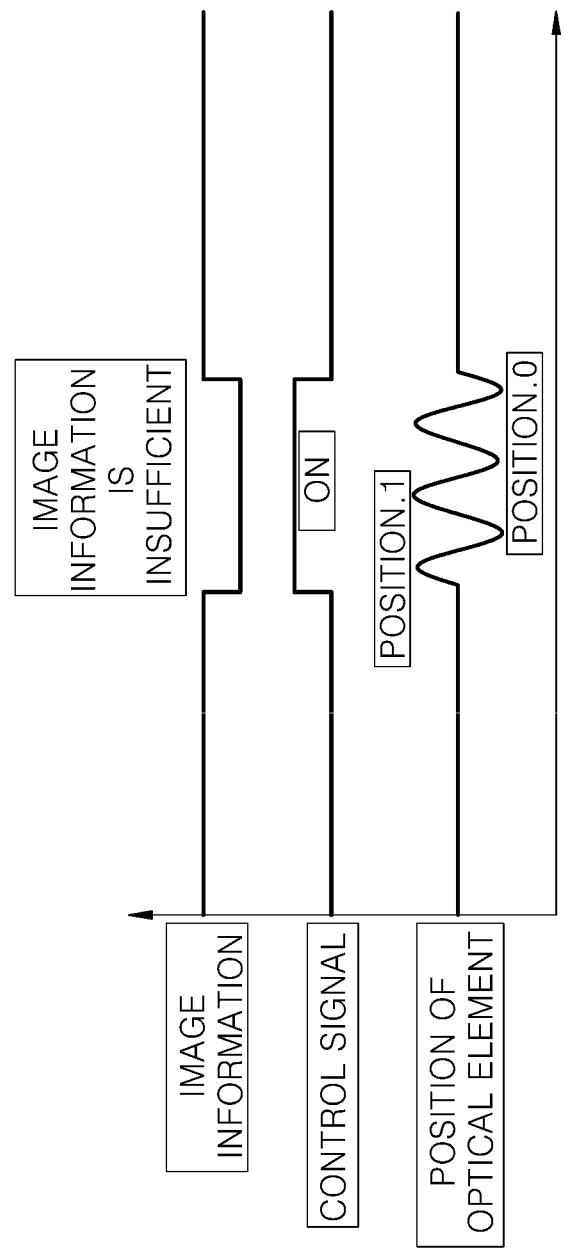

THREE-DIMENSIONAL INTRAORAL SCANNER

TECHNICAL FIELD

The present disclosure relates to a three-dimensional intraoral scanner, and more specifically, to a three-dimensional intraoral scanner, which may be produced to be slim so as to be easily insertable into the oral cavity of a patient, and may obtain the three-dimensional data within the oral cavity more accurately through at least one camera.

BACKGROUND ART

Generally, in a dental clinic or the like, the damaged teeth of a patient is treated by the impression taking process which produces a plaster cast for the teeth of the patient.

As described above, in the impression taking process which produces the plaster cast, there may occur problems such as the material consumption and cross-infection, breakability and preservation problems, and the like of the produced cast.

Particularly, by manually getting the impression for the damaged teeth of the patient using an impression material, there is a problem of not providing an accurate production figure when a prosthetics is produced.

That is, it is not possible to confirm the degree of error for the three-dimensional information of the produced prosthetics, and for such a reason, there is a problem in that the actually produced prosthetics does not match within the oral cavity of the patient.

Therefore, in recent years, there is a need for the development for a technology capable of accurately obtaining the three-dimensional information for the damaged teeth without using the impression material, thereby producing the prosthetics with the accurate figure.

Korean Patent Application Laid-Open No. 10-2014-0077380 (published on Jun. 24, 2014) (hereinafter, referred to as 'the related art') discloses the three-dimensional scanner, which obtains the three-dimensional intraoral data by inserting a part of the three-dimensional scanner into the oral cavity of the patient to analyze the patterns radiated into the oral cavity through the pattern provider.

However, in the related art, there is a problem in that it is possible to obtain only the three-dimensional data within the oral cavity by the pattern analysis, but it is not possible to accurately confirm the state of the oral cavity (bad tooth, tooth cracking and broken phenomenon, or the like) of the patient, and further, there is inconvenience in that the thickness of the portion inserted into the oral cavity of the patient is large, such that the patient should open his/her mouth wide when the oral cavity is scanned.

Further, the related art has the spatial constraint when the rear surface (i.e., the throat side) and the side surface (i.e., between the teeth and the inside of the lips) inside the oral cavity of the patient are measured.

DISCLOSURE

Technical Problem

An object of the present disclosure is to provide a three-dimensional intraoral scanner, which may actively rotate an optical element to adjust an angle of the optical element with respect to a portion having the spatial constraint when the oral cavity of a patient is measured, thereby obtaining the three-dimensional data of a specific portion even without moving the entire case.

Another object of the present disclosure is to provide a three-dimensional intraoral scanner, which may produce a portion inserted into the oral cavity of a patient to have the minimum volume and the minimum thickness, thereby overcoming the spatial constraint and minimizing the discomfort of the patient in obtaining the three-dimensional intraoral data from the patient.

Still another object of the present disclosure is to provide a three-dimensional intraoral scanner, which may easily obtain the three-dimensional intraoral data including image status information inside the oral cavity of the patient through two cameras disposed to be spaced apart from each other.

The technical objects of the present disclosure are not limited to the aforementioned technical objects, and other technical objects not mentioned will be clearly understood by those skilled in the art from the following descriptions.

Technical Solution

A three-dimensional intraoral scanner according to an exemplary embodiment of the present disclosure for achieving the objects includes: a case drawn in and out of the oral cavity, and formed with an opening opened such that the appearance (hereinafter, referred to as 'the image') inside the oral cavity is introduced into the case in the form of light through one end of the case, at least one camera disposed inside the case, and disposed to allow the light introduced through the opening of the case to pass, a light projector disposed on one side of the at least one camera to radiate light through the opening, an optical element provided to be tilted and rotated while reflecting or refracting the path of the light of the at least one camera and the light projector inside the case, and a light path change unit for moving the optical element to be adjustable.

Here, the light path change unit may include: a driving unit electrically driven and a driving force delivery unit for delivering the driving force generated by the driving unit to the optical element.

Further, the driving unit may include: any one of a motor, a piezo, a MEMS, and a solenoid.

Further, the piezo may include: a bending unit connected to the optical element and provided to be bent by providing a voltage.

Further, the light path change unit may include: a driving unit for generating a linear driving force for tilting and rotating the optical element and a driving force delivery unit for delivering the linear driving force generated by the driving unit to the optical element, in which the driving force delivery unit may be provided in the form of the connection bar connecting the driving unit to the optical element.

Further, the light path change unit may include: a driving unit for generating a linear driving force for tilting and rotating the optical element and a driving force delivery unit for delivering the linear driving force generated by the driving unit to the optical element, in which the driving force delivery unit may be provided in the form of the hinge connection link connecting the driving unit to the optical element.

Further, the case may include: a main body case provided with an image acquisition unit and a tip case provided with the optical element, in which the driving unit may be provided inside the main body case.

Further, the driving unit and the driving force delivery unit may be connected in a detachably coupling method.

Further, the driving unit and the driving force delivery unit may be connected in a magnetically coupling method.

Further, the driving unit and the driving force delivery unit may be connected in a fixedly coupling method.

Further, the light path change unit may allow the optical element to perform the rotation motion to adjust the introduction path of the light.

Further, the light path change unit may allow the optical element to perform the linear motion to adjust the introduction path of the light.

Further, the three-dimensional intraoral scanner may further include: an angle adjustment unit for controlling an adjustment angle upon the rotation motion of the optical element.

Further, the three-dimensional intraoral scanner may further include: a movement amount control unit for controlling an amount of movement upon the linear motion of the optical element.

Further, the three-dimensional intraoral scanner may further include: an adjustment amount range control unit for determining and controlling the range of the adjustment angle or the amount of movement for each device.

Further, the three-dimensional intraoral scanner may further include: an interlocking adjustment unit for interlocking and adjusting the light path change unit and the at least one camera.

Further, the interlocking adjustment unit may allow the light path change unit to consecutively adjust the optical element to be changed by a plurality of preset light path change amounts.

A three-dimensional intraoral scanner according to another embodiment of the present disclosure for achieving the objects includes: a case drawn in and out of the oral cavity, and formed with an opening opened such that the appearance (hereinafter, referred to as 'the image') inside the oral cavity is introduced into the case in the form of light through one end of the case, at least one camera disposed inside the case, and disposed to allow the light introduced through the opening of the case to pass, a light projector disposed on one side of the at least one camera to radiate light through the opening, an optical element provided to be tilted and rotated while reflecting or refracting the path of the light of the at least one camera and the light projector inside the case, a light path change unit for moving the optical element to be adjustable, and an interlocking adjustment unit for controlling to interlock and adjust the operation of the light path change unit and the at least one camera in order to move the optical element to be adjustable, wherein the interlocking adjustment unit controls to tilt the optical element, if it is determined that the image data obtained by the introduction of the light are insufficient.

Advantageous Effects

The present disclosure may achieve various effects as follows according to the three-dimensional intraoral scanner according to the exemplary embodiment of the present disclosure.

First, it is possible to measure the portion where it is somewhat difficult to measure due to the spatial constraint inside the oral cavity of the patient by adjusting the angle of the optical element or the position of the optical element, thereby easily measuring the portion.

Second, it is possible to produce the portion inserted into the oral cavity of the patient to be slim, thereby eliminating the discomfort of the patient in the process of obtaining the three-dimensional intraoral data.

Third, it is possible to obtain more accurate and reliable three-dimensional intraoral data by integrating the appearance (image) image within the oral cavity obtained by at least one camera.

Fourth, it is possible to provide the main body case such that the upper case provided in the simply detachable method may be separated from the lower case, thereby very easily replacing the internal component of the case.

Fifth, it is possible to easily obtain the insufficient three-dimensional image data by the operation of the light path change unit, thereby saving the scanning time of the operator.

DESCRIPTION OF DRAWINGS

FIG. 19 is a graph illustrating a process of automatically obtaining the three-dimensional data in all sections using a three-dimensional intraoral scanner according to another exemplary embodiment of the present disclosure.

BEST MODE

Figure 1:
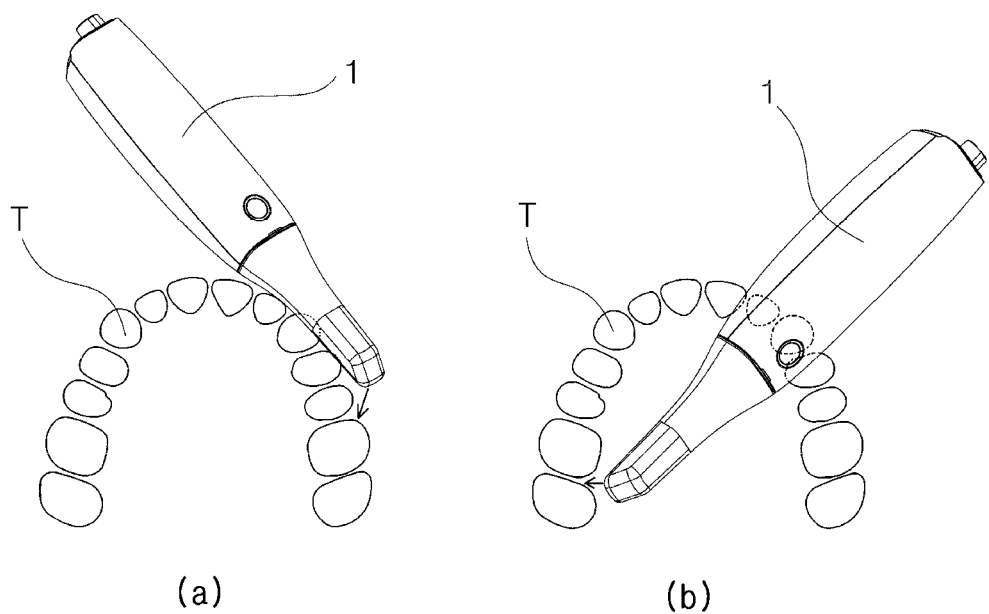
FIG. 1 is a conceptual diagram illustrating an oral cavity scan appearance using a three-dimensional intraoral scanner according to the present disclosure.

Hereinafter, some exemplary embodiments of the present disclosure will be described in detail through exemplary drawings. In adding reference numerals to the components in each drawing, it should be noted that the same components are denoted by the same numerals as possible even if they are indicated in different drawings. Further, in describing the exemplary embodiment of the present disclosure, if it is determined that a detailed description of a related known configuration or function obstructs the understanding of the exemplary embodiment of the present disclosure, the detailed description thereof will be omitted.

In describing the components of the exemplary embodiment of the present disclosure, terms such as first, second, A, B, (a), and (b) may be used. These terms are only for distinguishing the component from other components, and the nature, order, or sequence of the component is not limited by the terms. Further, unless otherwise defined, all terms used herein, including technical or scientific terms, have the same meaning as commonly understood by those skilled in the art to which the present disclosure pertains. Terms as defined in a commonly used dictionary should be interpreted as having a meaning consistent with the meaning of the related technology on the context and should not be interpreted as an ideal or excessively formal meaning unless explicitly defined in the present application.

Figure 2:
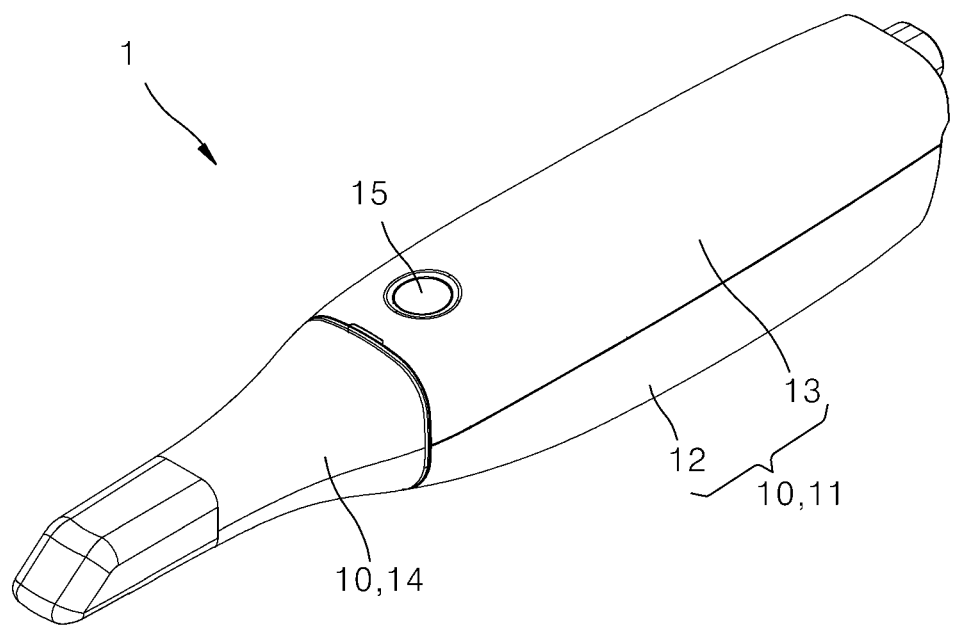
FIG. 2 is a perspective diagram illustrating a three-dimensional intraoral scanner according to an exemplary embodiment of the present disclosure.
Figure 3:
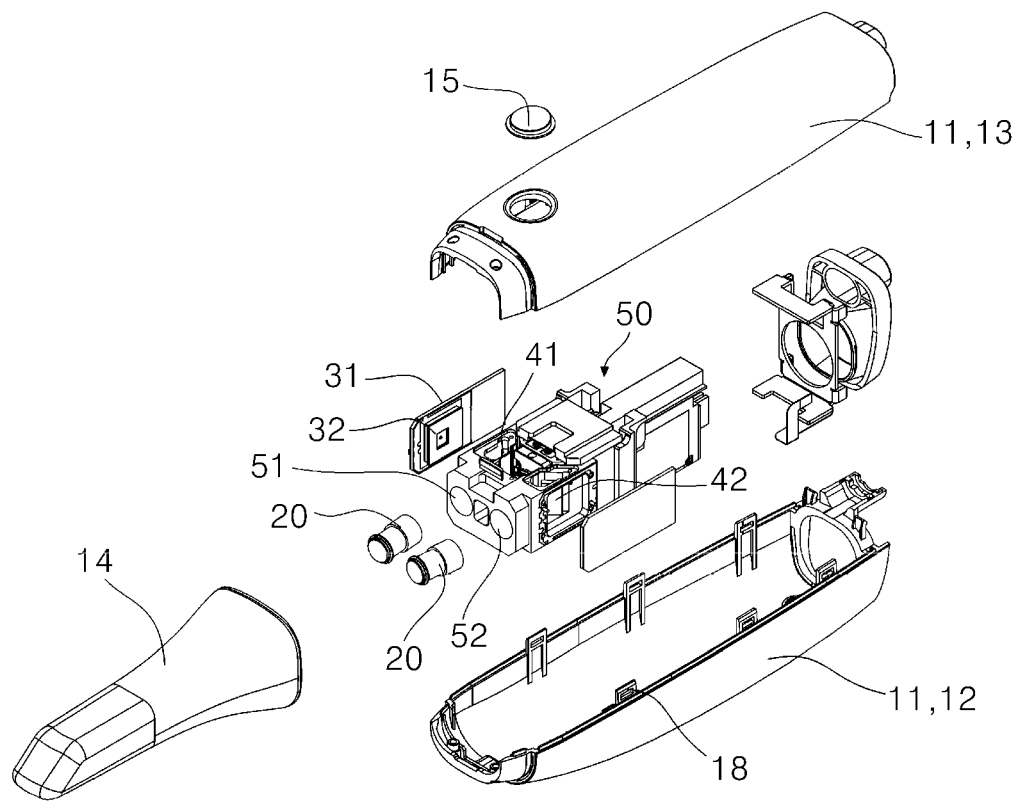
FIG. 3 is an exploded perspective diagram of FIG. 2.
Figure 4:
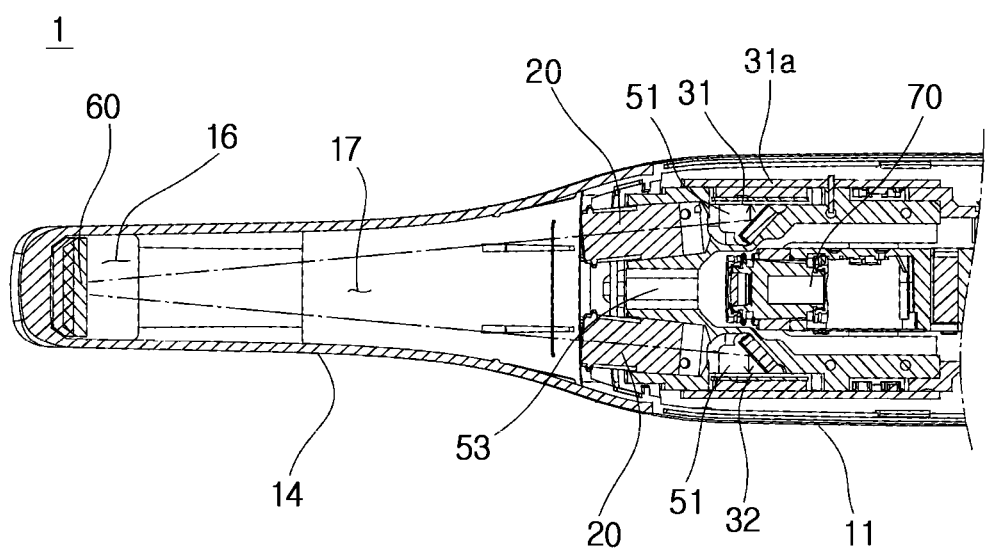
FIG. 4 is a cut-out perspective diagram taken along the line A-A' illustrated in FIG. 2.

FIG. 1 is a conceptual diagram illustrating an oral cavity scan appearance using a three-dimensional intraoral scanner according to the present disclosure, FIG. 2 is a perspective diagram illustrating the three-dimensional intraoral scanner according to an exemplary embodiment of the present disclosure, FIG. 3 is an exploded perspective diagram of FIG. 2, and FIG. 4 is a cut-out perspective diagram taken along the line A-A' illustrated in FIG. 2.

As illustrated in FIG. 1, a three-dimensional intraoral scanner 1 according to an exemplary embodiment of the present disclosure is one of a scanning apparatus for obtaining the inside of the oral cavity of a patient, particularly, a teeth structure as the three-dimensional data.

The three-dimensional intraoral scanner 1 according to the exemplary embodiment of the present disclosure illustrated in FIG. 1 may easily obtain the three-dimensional data of the entire inside of the oral cavity even when performing the scanning after inserting only a portion of a tip case 14 to be described later into the oral cavity of a patient.

Particularly, the three-dimensional intraoral scanner according to the exemplary embodiment of the present disclosure proposes a structure of very easily obtaining the three-dimensional data for a portion between teeth (T) and a lips (not illustrated) inside the oral cavity of the patient illustrated in FIG. 1A and the three-dimensional data for the teeth portions close to a throat side inside the oral cavity of the patient illustrated in FIG. 1B. This will be specifically described later, and first, the internal structure of the components for scanning according to the three-dimensional intraoral scanner 1 according to the exemplary embodiment of the present disclosure will be specifically described.

As illustrated in FIGS. 2 to 4, the three-dimensional intraoral scanner 1 according to the exemplary embodiment of the present disclosure includes a case 10 which may be drawn in and out of the oral cavity.

An image acquisition unit 20 including at least one camera may be disposed inside the case 10. The image acquisition unit 20 is disposed inside the case 10 to serve to obtain the image data inside the oral cavity introduced into the case in the form of light.

Here, the at least one camera may be disposed inside the case 10 to allow the light incident from one end of the case 10 to pass through a predetermined path. The 'light' transmitting the image acquisition unit 20 provided as the at least one camera means a visible light region which may be seen by the human eyes, and refers to the appearance (hereinafter, abbreviated 'image') inside the oral cavity of the patient to be measured.

Meanwhile, the at least one camera may be provided as a single camera inside the case 10, and may also be provided as a stereo camera having two cameras disposed to be spaced apart from each other in the width direction, respectively, inside the case 10.

As illustrated in FIG. 4, the case 10 may be provided with an opening 16 opened such that the image is introduced into the case 10 in the form of light through one end of the case 10. The opening 16 may be an inlet through which the light outside the case 10 is introduced into the case 10. Since the emission light and the incident light need to be transmitted through the opening 16, the opening 16 may be provided with a transparent plate (not illustrated) made of a transparent material, thereby preventing the foreign matters from being introduced from the outside. The light incident through the opening 16 transmits the single camera or the stereo camera through the respective different light paths, respectively. The light transmitting the camera may be accommodated by imaging sensors 31b, 32b provided in imaging boards 31a, 32a to be described later, and generate the respective image information in the imaging sensors 31b, 32b.

Here, the image means the image data obtained using at least one camera, and may be analyzed by an operation unit to be described later and changed into the three-dimensional image data as three-dimensional geometry information inside the oral cavity. Further, when two image data are simultaneously obtained if the camera is provided as the stereo camera, the image may be likewise changed into the three-dimensional image data of the image when a separation distance between the stereo camera provided as the pair of cameras by the operation unit to be described later and a focal distance at a target point captured by each camera are known.

Here, each of at least one camera may include at least two transmission lenses capable of adjusting the focus on the image within the oral cavity.

To obtain the three-dimensional image data, the three-dimensional intraoral scanner 1 according to the exemplary embodiment of the present disclosure may further include the imaging boards 31a, 32a having the imaging sensors 31b, 32b for imaging-processing the light transmitting the camera, respectively.

If the camera is provided as the single camera, the imaging board may also be provided as a single board, and if the camera is provided as the stereo camera having two cameras, the imaging board may also be provided to have one-to-one correspondence with each camera.

Meanwhile, the three-dimensional intraoral scanner according to the exemplary embodiment of the present disclosure may further include the operation unit for generating three-dimensional geometry information of the internal shape of the oral cavity by analyzing the image data obtained by the camera.

As described above, the operation unit may serve to convert the inside of the oral cavity into data as the three-dimensional geometry information by analyzing the image data obtained by the image acquisition unit 20 provided as at least one camera.

As illustrated in FIGS. 1 to 3, the case 10 serves to provide a predetermined space such that the image acquisition unit 20 provided as at least one camera and the imaging board 31 are embedded therein.

More specifically, as illustrated in FIG. 2, the case 10 includes a main body case 11 composed of a lower case 12 formed with a predetermined space in which the components are embedded, and an upper case 13 provided on the top of the lower case 12 and detachably coupled to the lower case 12 to cover the components.

As illustrated in FIG. 3, the lower case 12 and the upper case 13 may be coupled to each other by the operation in which a hook unit (not illustrated) formed on the upper case 13 is locked to a hook locking unit 18 formed on the lower case 12 when being vertically in close contact with each other, respectively.

Further, the case 10 may further include the tip case 14 detachably coupled to the main body case 11, formed with the aforementioned opening 16, and formed with an incident/emission light path unit 17 for guiding the light incident into the main body case 11 through the opening 16 and the light emitted from the inside of the main body case 11 through the opening 16.

Here, the light incident into the main body case 11 through the opening 16 (hereinafter, referred to as 'incident light') means the image which is the appearance inside the oral cavity of the patient, and the light emitted from the inside of the main body case 11 through the opening 16 (hereinafter, referred to as 'emission light') means the radiation light radiated from a light projector 70 to be described later.

The internal structure of the tip case 14 may be formed in a light guide structure in which the incident light and the emission light are easily radiated inside and outside the case 10. Further, the opening 16 may be formed to be open in one side direction perpendicular to the longitudinal direction of the tip case 14, and an optical element 60 controlled by a light path change unit 80 to be described later may be disposed in the opening 16.

As described above, one end of the camera may be disposed to be converged in the tip case 14 side when the camera is provided as the stereo camera, and disposed to be overlapped with the tip case 14 side by a predetermined distance. Further, the other end of the camera may be provided to be connected to a camera mounting unit 50 fixed inside the main body case 11.

Meanwhile, as illustrated in FIGS. 2 to 4, the three-dimensional intraoral scanner 1 according to the exemplary embodiment of the present disclosure may further include the light projector 70 disposed inside the case 10 and for emitting predetermined emission light through between the pair of cameras, and radiating the emission light through the opening 16 formed in one end of the case 10.

The three-dimensional intraoral scanner 1 according to the exemplary embodiment of the present disclosure may have an optimal placement structure in which the aforementioned components are disposed inside the case 10, in which the main body case 11 is formed in the minimum thickness even while forming the tip case 14 as long and slim as possible so as to be easily drawn in and out of the oral cavity of the patient. Therefore, the three-dimensional intraoral scanner 1 according to the exemplary embodiment of the present disclosure may be easily inserted into the portions of the rear surface (i.e., the throat side) and the side surface (i.e., between the teeth and the inside of the lips) having the serious spatial constraint inside the oral cavity of the patient.

More specifically, in the case 10, as illustrated in FIG. 3, one end of the camera is provided to protrude toward the tip case 14 and the other end of the camera is inserted and installed, and further, a camera mounting unit 50 formed with a light waveguide, which is the path of the incident light transmitting the camera or the emission light radiated from the light projector 70, may be disposed.

The light waveguide formed on the camera mounting unit 50 may be provided in the form of darkroom such that the incident light incident from the opening 16 and the emission light radiated from the light projector 70 are separated from each other not to affect each other.

Figure 5:
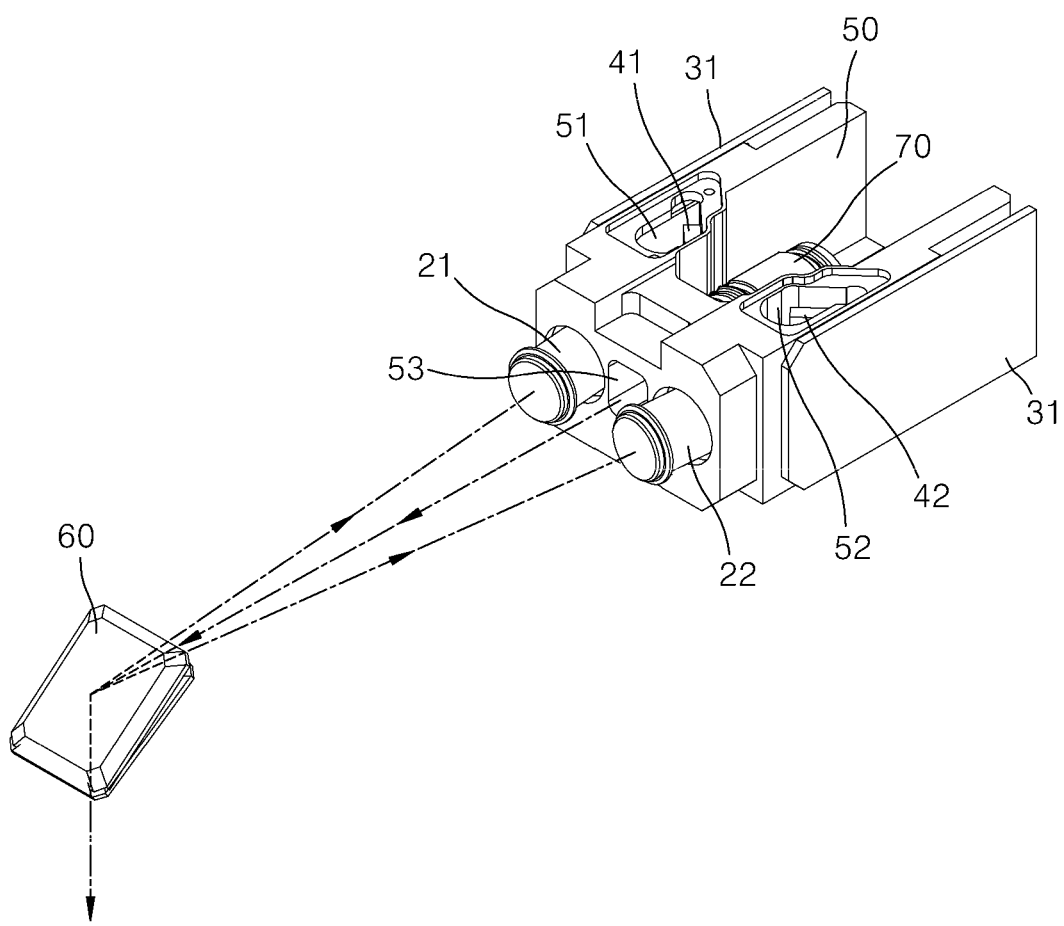
FIG. 5 is a perspective diagram illustrating a light path using a pair of cameras among the components illustrated in FIG. 2.
Figure 6:
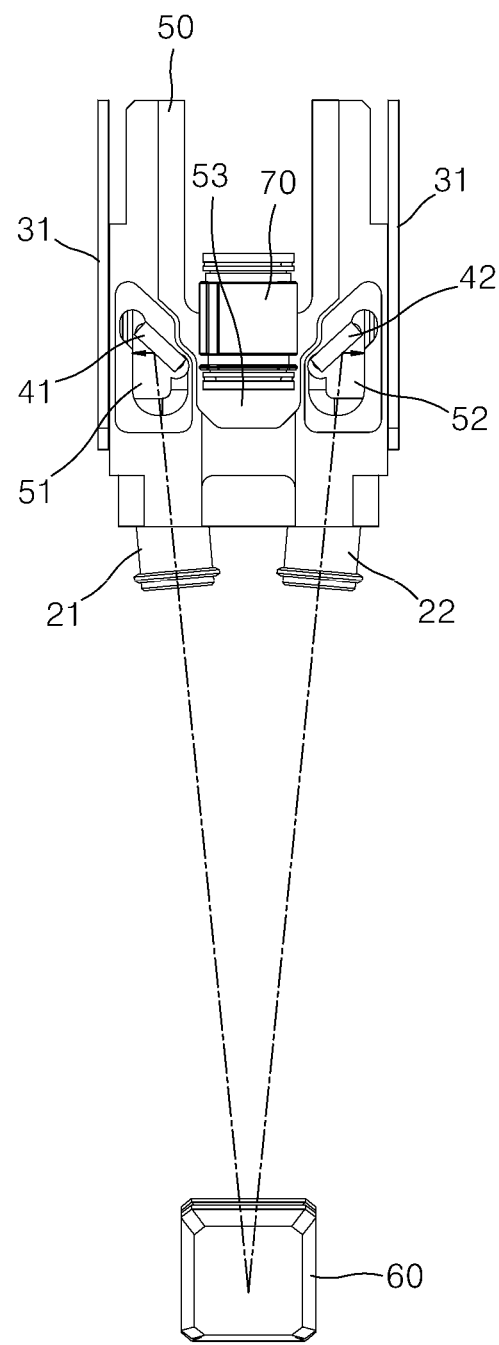
FIG. 6 is a plan diagram of FIG. 5.
Figure 7:
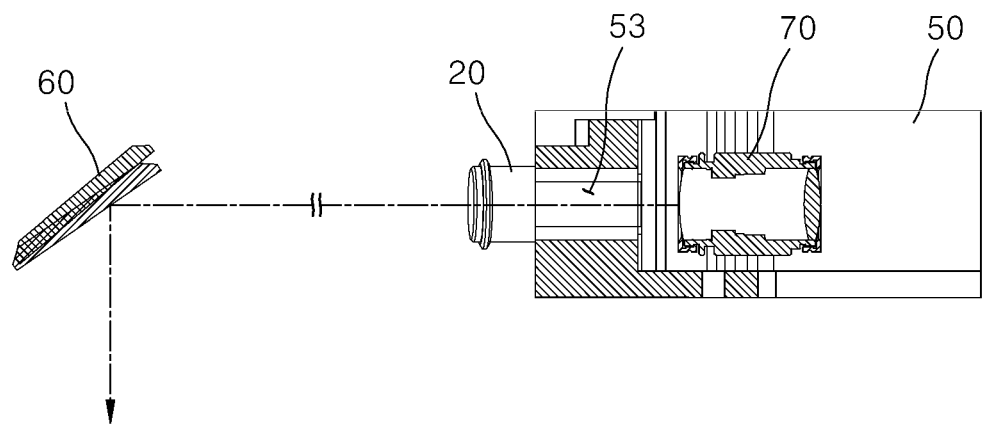
FIG. 7 is a cross-sectional diagram taken along the line B-B illustrated in FIG. 5.
Figure 8:
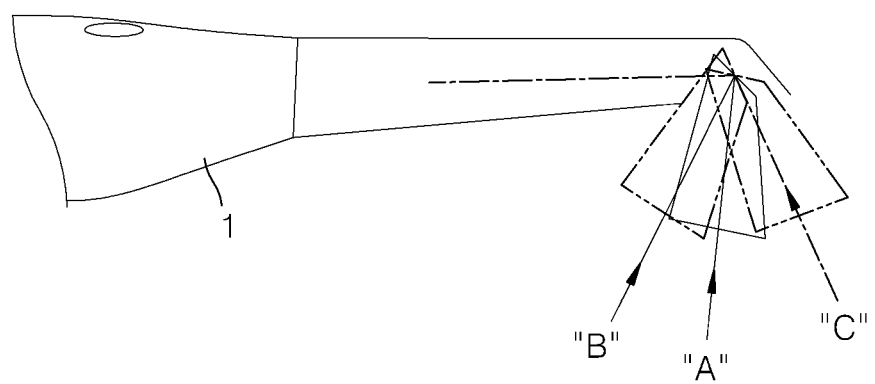
FIG. 8 is a conceptual diagram illustrating various incident appearances of the incident light according to the rotational state of an optical element among the components illustrated in FIG. 2.

FIG. 5 is a perspective diagram illustrating a light path using a pair of cameras among the components illustrated in FIG. 2, FIG. 6 is a plan diagram of FIG. 5, FIG. 7 is a cross-sectional diagram taken along the line B-B illustrated in FIG. 5, and FIG. 8 is a conceptual diagram illustrating various incident patterns of the incident light according to the rotational state of an optical element among the components illustrated in FIG. 2.

As illustrated in FIGS. 5 to 8, the three-dimensional intraoral scanner according to the exemplary embodiment of the present disclosure may further include the light path change unit 80 disposed inside the case 10 to adjust the path of the light incident into the case 10 during driving.

Specifically, the light path change unit 80 may change the path of the light incident through the opening 16 formed in the tip case 14 of the case 10.

Further, the light path change unit 80 may include the optical element 60 including a mirror capable of reflecting the path of the light or a prism capable of refracting the path of the light.

Hereinafter, to prevent the confusion of understanding, the light path change unit 80 is collectively called as the optical element 60, but used as the concept including the prism for refracting the path of the light as well as the mirror for reflecting the path of the light.

The optical element 60 serves to reflect or refract the incident light incident into the main body case 11 and the emission light emitted from the inside of the main body case 11 to a predetermined path using the light path change unit 80.

More specifically, the optical element 60 may be rotatably provided with respect to a predetermined axis inside the opening 16 formed in the tip case 14. Here, the predetermined axis may be defined as, for example, the horizontal axis horizontally formed in the left/right width directions of the tip case 14, if the opening 16 is formed to communicate with the outside from the front end of the tip case 14 downward perpendicular to the longitudinal direction of the tip case 14 in FIG. 5.

The installation appearance of the optical element 60 and the light path change unit 80 for driving the same inside the tip case 14 will be specifically described later.

The thus formed optical element 60 may change an angle of the incident light incident through the opening 16 by the rotational operation of one of the upper end and lower end of the optical element 60 around the predetermined axis, thereby substantially changing the scan region of the image captured by at least one camera.

Here, as illustrated in FIG. 8, when the scan region is changed into one of "A", "B", and "C", the center axis of the emission light radiated from the light projector 70 via the optical element 60 and the center axis of the incident light incident via the optical element 60 are also changed according to the tilting rotation of the optical element 60, and these center axes are not illustrated in the drawing, but may be moved while forming a virtual arc formed according to the tilting rotation of the reflection surface of the optical element 60.

Therefore, the three-dimensional intraoral scanner 1 according to the exemplary embodiment of the present disclosure may obtain more precise and reliable three-dimensional image data corresponding to the rear surface (i.e., the throat side) and the side surface (i.e., between the teeth and the inside of the lips) conventionally having the serious spatial constraint in terms of the measurement space inside the oral cavity of the patient.

Figure 9:
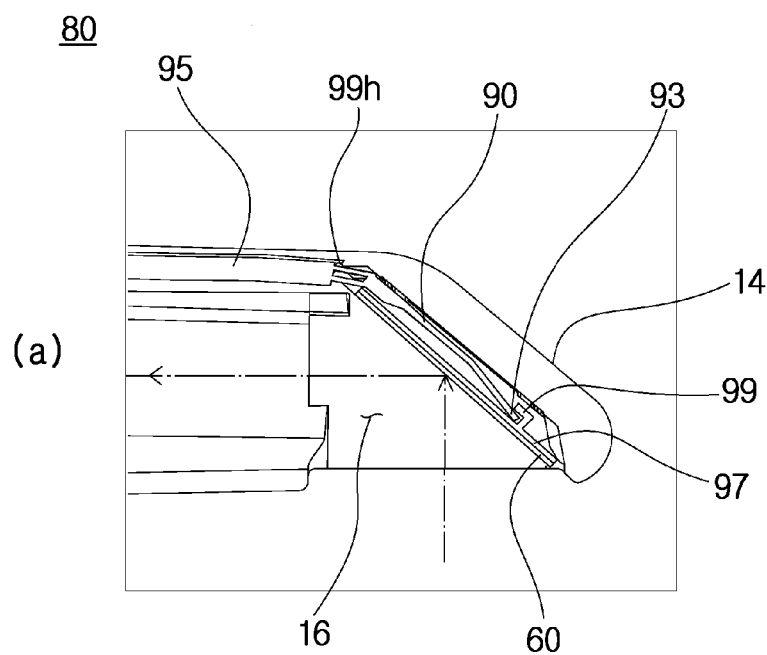
FIG. 9 is a partial cross-sectional diagram illustrating an operation state of a first optical element rotary means among the components of the three-dimensional intraoral scanner according to the exemplary embodiment of the present disclosure.
Figure 9:
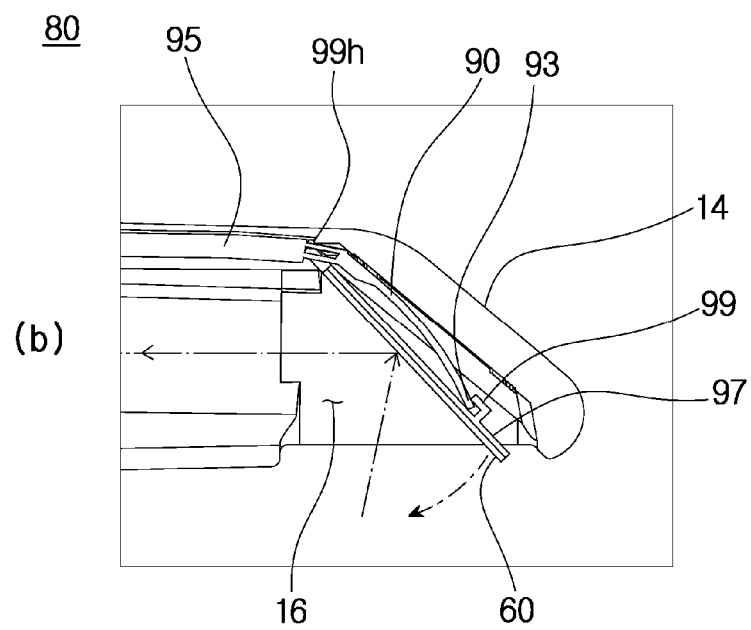

FIG. 9 is a partial cross-sectional diagram illustrating an operation state of a light path change unit among the components of the three-dimensional intraoral scanner according to the exemplary embodiment of the present disclosure.

The light path change unit 80 may be implemented as a first light path change unit 80 to be described later. That is, the first light path change unit 80 may include a driving unit 90 electrically driven, and a driving force delivery unit 97 for delivering the driving force generated by the driving unit 90 to the optical element 60.

Here, any configuration may be adopted as the driving unit 90 as long as it is electrically driven. Further, the driving force delivery unit 97 may be provided in the form of the rotation frame rotatably fixing and supporting the optical element 60.

Meanwhile, as illustrated in FIGS. 9A and 9B, the driving unit 90 may be a piezoelectrically coated piezo provided to be bendable so as to be bent by the asymmetric contraction and the asymmetric expansion according to the voltage supply.

More specifically, as illustrated in FIGS. 9A and 9B, The driving unit 90 provided as the piezo may be connected to an electric wire 95 such that the driving unit may receive power, and the driving unit 90 is piezoelectrically coated as described above.

As illustrated in FIG. 9A, a front end 93 of the driving unit 90 provided as the piezo may be fixed to the back surface of the driving force delivery unit 97 provided in the form of the rotation frame in which the optical element 60 is rotatably fixed and installed.

More specifically, the driving force delivery unit 97 provided in the form of the rotation frame may be provided to have one end coupled by a hinge 99*h* to the top of the opening 16 inside the tip case 14, and the other end rotated in the bottom front portion of the opening 16. Here, the back surface of the driving force delivery unit 97 may be formed with a fixing hook 99 such that the front end of the driving unit 90 is inserted to be locked and fixed.

Here, when the driving unit 90 receives the voltage by the electric wire 95, the piezoelectrically coated portion is contracted or expanded and rotated backward around the aforementioned one end coupled by the hinge 99*h*, as illustrated in FIG. 9B, thereby changing the incident angle of the incident light through the opening 16.

However, the scope of the present disclosure should not necessarily be limited to the driving unit 90 provided as the single piezo. That is, the three-dimensional intraoral scanner according to the exemplary embodiment of the present disclosure may be provided such that the driving unit 90 provided as the piezo is bent on a single portion, but provided such that the driving unit 90 is bendable at two portions to be mutually symmetric to the back surface of the driving force delivery unit 97, and the two bending portions may also be mutually operated alternately to change a rotational angle of the optical element 60.

Meanwhile, although not illustrated in the drawing, as the driving unit, one of a micro-electro mechanical system (MEMS) and a solenoid other than the aforementioned piezo may also be adopted.

Figure 10A:
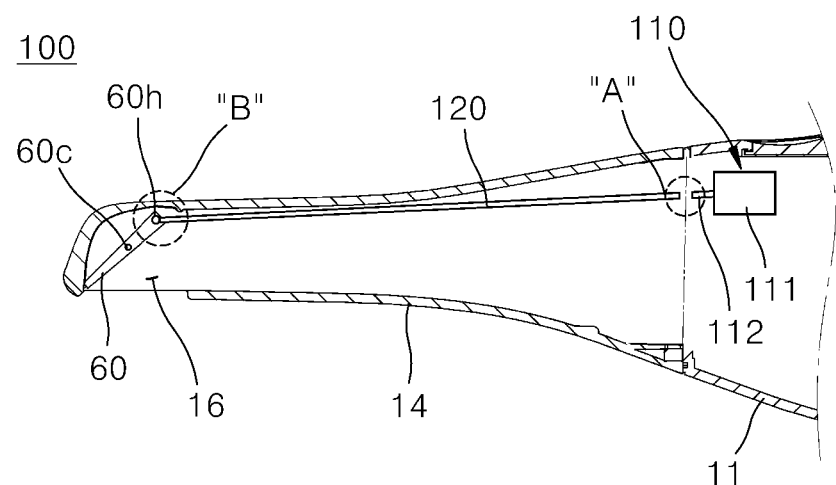
FIGS. 10A and 10B are operational cross-sectional diagrams illustrating various forms of a second light path change unit among the components of the three-dimensional intraoral scanner according to the exemplary embodiment of the present disclosure.
Figure 10B:
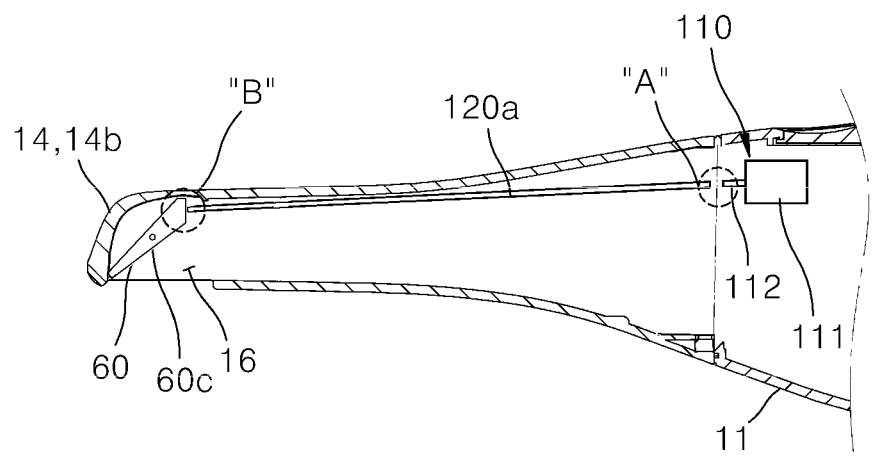

FIGS. 10A and 10B are operational cross-sectional diagrams of various forms of a second light path change unit among the components of the three-dimensional intraoral scanner according to the exemplary embodiment of the present disclosure.

In the three-dimensional intraoral scanner according to the exemplary embodiment of the present disclosure, as illustrated in FIGS. 10A and 10B, a second light path change unit 100 is provided as a linear motor 111 provided with a movable shaft 112 around which a driving unit 110 is moved in the liner direction.

Here, if the driving unit 110 is provided as the linear motor 111, the driving unit 110 has a relatively large volume whereas the tip case 14 is produced to be slim due to the aforementioned reason and thus the internal space thereof is very narrow, such that the driving unit 110 is preferably positioned between the lower case 12 and the upper case 13, that is, inside the main body case 11. At this time, since the distance between the driving unit 110 and the optical element 60 is somewhat spaced, a driving force delivery unit 120 for delivering the driving force of the driving unit 110 may be adopted in the form of the connection bar.

As illustrated in FIG. 10A, the driving force delivery unit 120 may also be provided to receive the linear driving force of the driving unit 110 in a first connection portion (see the reference numeral "A") such that the optical element 60 receives the linear driving force in the linear direction in a second connection portion (see the reference numeral "B").

In the first connection portion "A", the rear end of the driving force delivery unit 120 may be mutually connected to the movable shaft 112 of the linear motor 111 in one method of a fixedly coupling method and a detachably coupling method.

Likewise, in the second connection portion "B", the front end of the driving force delivery unit 120 may be mutually connected to the optical element 60 in one method of the fixedly coupling method and the detachably coupling method.

As the representative example of the fixedly coupling method, there may be a coaxial coupling, a welding coupling, a hinge coupling, or the like. As an example of the detachably coupling method, there may be a hook coupling, a forcibly coupling, a magnetic coupling, or the like. If the driving force delivery unit 120 and the driving unit 110, and the driving force delivery unit 120 and the optical element 60 are to be coupled in the detachably coupling method in the first connection portion "A" and the second connection portion "B", respectively, the relationship about the mutual repulsive force and attractive force between a magnet and a magnetic body, which are the magnetic coupling elements, should be first established.

As described above, if the first connection portion "A" and the second connection portion "B" are to be coupled in the detachably coupling method, there are advantages in that the separate assembling and separation are not required and the replacement and the repair are simply possible in the detachable method, when the tip case 14 or the optical element 60 is replaced or repaired.

In the three-dimensional intraoral scanner according to the exemplary embodiment of the present disclosure, as illustrated in FIG. 10A, the driving force delivery unit 120 may adopt the detachably coupling method in the first connection portion "A", and adopt the fixedly coupling method in the second connection portion "B", and as illustrated in FIG. 10B, adopt the detachably coupling method in all of the first connection portion "A" and the second connection portion "B".

Referring to FIG. 10A, if the fixedly coupling method is adopted in the first connection portion "A" and the second connection portion "B" (hereinafter, referred to as 'first delivery structure'), when the movable shaft 112 is moved forward by a predetermined length by the driving operation of the linear motor 111 of the driving unit 110, the upper end of the optical element 60 coupled by a hinge 60h through the second connection portion "B" is rotated forward by a predetermined angle around a predetermined axis 60c while the connection bar, which is the driving force delivery unit 120, is directly moved forward through the first connection portion "A", and when the movable shaft 112 is moved backward by a predetermined length by the driving operation of the linear motor 111 of the driving unit 110 in the opposite direction, the upper end of the optical element 60 coupled by the hinge 60h through the second connection portion "B" is rotated backward by a predetermined angle around the predetermined axis 60c while the connection bar, which is the driving force delivery unit 120, is directly moved backward through the first connection portion "A".

Meanwhile, referring to FIG. 10A, a case where the detachably coupling method is adopted in the first connection portion "A", and the fixedly coupling method is adopted in the second connection portion "B" may be assumed (hereinafter, referred to as 'second delivery structure). To implement the detachably coupling method, one of a magnet for generating a predetermined magnetic force and a magnetic body operated by the magnetic force of the magnet may be provided on the movable shaft 112 of the driving unit 110, or one of the aforementioned magnet and magnetic body may be provided on the end corresponding to the first connection portion "A" of the driving force delivery unit 120.

Here, the rotational operation of the optical element 60 in the second connection portion "B" in which the fixedly coupling method is adopted is based on the aforementioned first delivery structure, such that the detailed description thereof will be omitted.

However, if the detachably coupling method is adopted as in the first connection portion "A", the driving force delivery method may be classified into a case of using 'the attractive force' and a case of using 'the repulsive force' generated according to the mutual magnetism.

In the case of using the attractive force, the linear driving force of the driving unit 110 may be delivered in the front and back direction by the mutual attractive force between the movable shaft 112 and the driving force delivery unit 120 in the first connection portion "A".

In the case of using the repulsive force, although not illustrated in the drawing, the present disclosure may be additionally provided with a restoring means for adding a restoring force allowing the driving force delivery unit 120 moved forward by the mutual repulsive force through the first connection portion "A" to be restored backward, which is the original position, if the repulsive force is released.

Meanwhile, referring to FIG. 10B, if the detachably coupling method is adopted in all of the first connection portion "A" and the second connection portion "B" (hereinafter, referred to as 'third delivery structure'), the delivery method of the linear driving force of the driving unit 110 in the first connection portion "A" is based on the second delivery structure, such that the detailed description thereof will be omitted.

However, if the detachably coupling method is adopted in the second connection portion "B", the tilting rotation method of the optical element 60 may be classified into a case of using 'the attractive force' and a case of using 'the repulsive force' generated according to the mutual magnetism between the driving force delivery unit 120 and the optical element 60.

In the case of using the attractive force, when the driving force delivery unit 120 is linearly moved forward by the mutual attractive force between the driving force delivery unit 120 and the optical element 60 in the second connection portion "B", the upper end of the optical element 60 is tilted and rotated forward by a predetermined angle while moved forward with respect to the predetermined axis 60c, and when the driving force delivery unit 120 is linearly moved backward, the upper end of the optical element 60 may be tilted and rotated backward by a predetermined angle while moved backward with respect to the predetermined axis 60c.

In the case of using the repulsive force, although not illustrated in the drawing, the present disclosure may be additionally provided with the restoring means for adding the restoring force allowing the optical element 60 tilted and rotated by a predetermined angle forward by the mutual repulsive force through the second connection portion "B" to be tilted, rotated, restored backward, which is the original position, if the repulsive force is released.

Here, as illustrated in FIG. 10A, the driving force delivery unit 120 may be coupled to the upper end of the optical element 60 via the hinge 60h, and when the linear driving force of the driving unit 110 is delivered to the optical element 60 through the first connection portion "A", the optical element 60 may be tilted and rotated by a predetermined angle around the predetermined axis 60c in the second connection portion "B".

Figure 11:
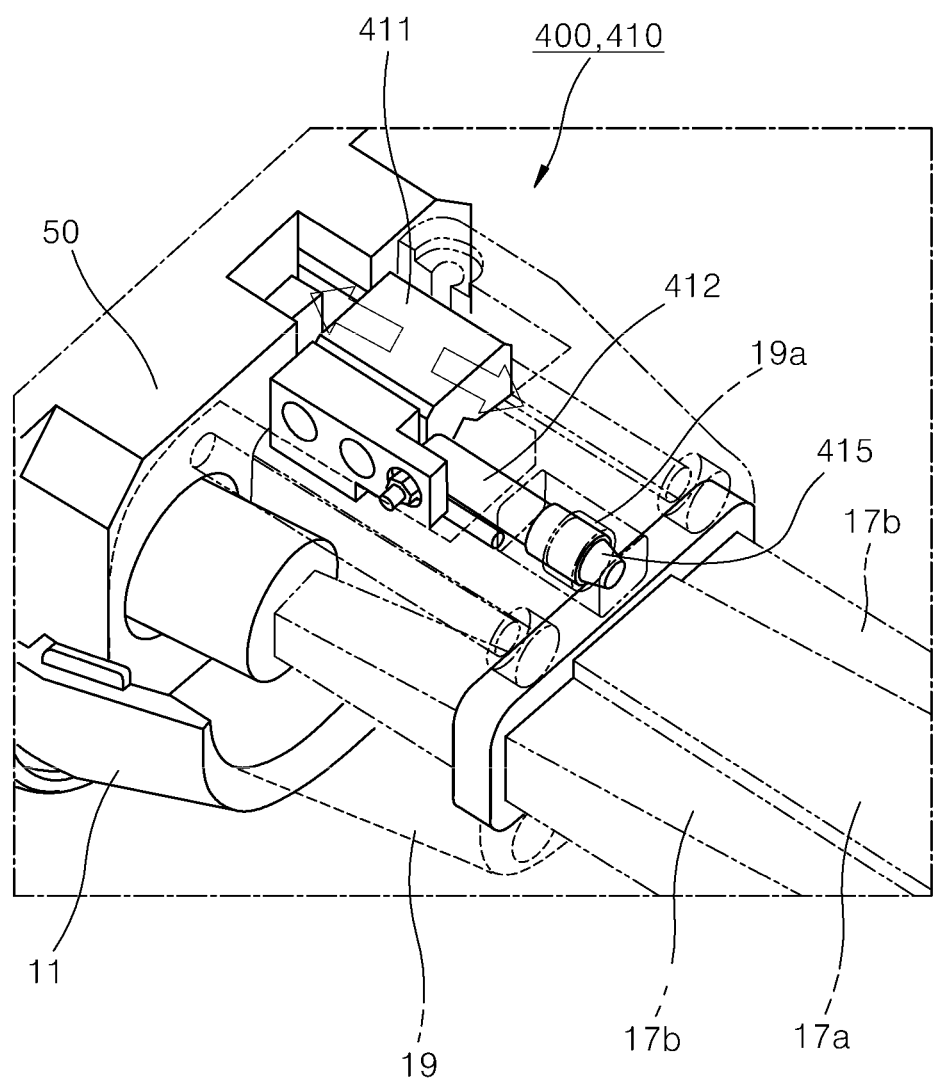
FIG. 11 is a partial projection perspective diagram illustrating a driving unit among the components of the second light path change unit illustrated in FIGS. 10A and 10B.
Figure 12:
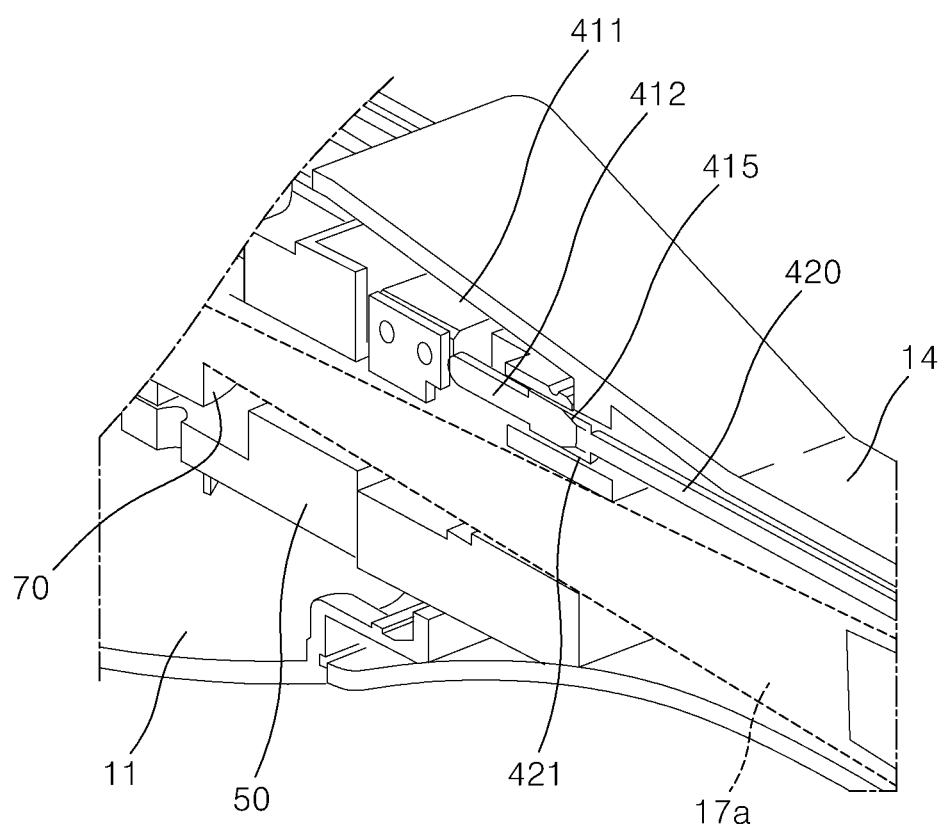
FIG. 12 is a partially cut-out perspective diagram illustrating the connection relationship of a driving force delivery unit connected to the driving unit illustrated in FIG. 11.
Figure 13:
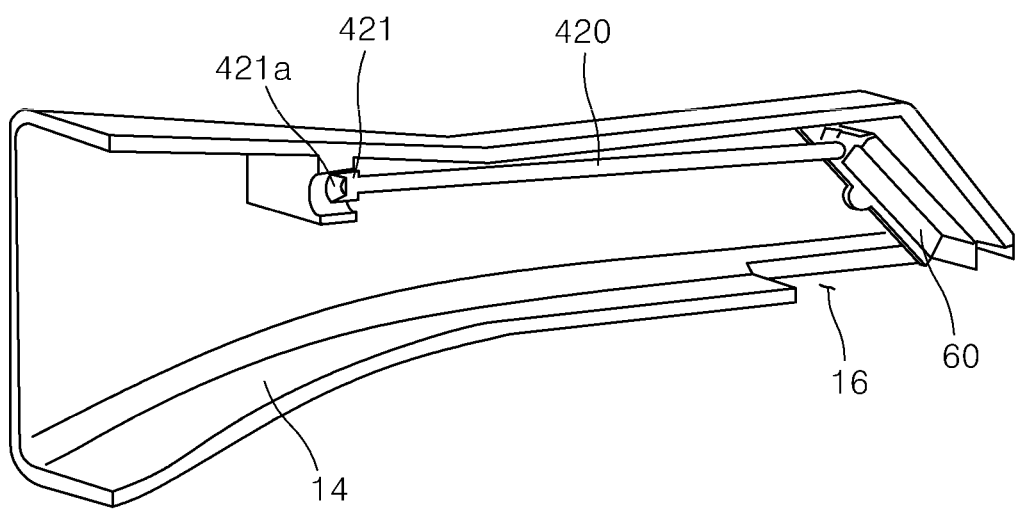
FIG. 13 is an internal perspective diagram illustrating the connection state with the optical element of the driving force delivery unit connected to the driving unit illustrated in FIG. 11.

FIG. 11 is a partial projection perspective diagram illustrating a driving unit among the components of the second light path change unit illustrated in FIGS. 10A and 10B, FIG. 12 is a partially cut-out perspective diagram illustrating the connection relationship of a driving force delivery unit connected to the driving unit illustrated in FIG. 11, and FIG. 13 is an internal perspective diagram illustrating the connection state with the optical element of the driving force delivery unit connected to the driving unit illustrated in FIG. 11.

The detailed description of the second light path change unit 100 among the components of the three-dimensional intraoral scanner according to the exemplary embodiment of the present disclosure will be described with reference to FIGS. 11 to 13 as follows. Hereinafter, the second light path change unit illustrated in FIGS. 11 to 13 is denoted using reference numeral 400 or more.

In the three-dimensional intraoral scanner according to the exemplary embodiment of the present disclosure, as illustrated in FIGS. 11 to 13, a second light path change unit 400 may include a driving unit 410 provided inside the main body case 11 to generate a linear driving force, and a driving force delivery unit 420 provided to extend toward the tip case 14 so as to receive the linear driving force generated by the driving unit 410 to tilt and rotate the optical element 60 and provided as the connection bar.

A connection block 19 for connecting the tip case 14 is provided to protrude from the front end of the main body case 11 to the outside, and the tip case 14 may be fixed and installed to the front end of the main body case 11 via the connection block 19.

The driving unit 410 includes a driving motor 411 electrically driven and provided on the connection block 19 side to be movable in the front and back direction, and a delivery shaft 412 moved by a predetermined distance in the front and back direction in conjunction with the driving motor 411.

The delivery shaft 412 may be disposed to penetrate a shaft hole 19a formed to penetrate the connection block 19 in the longitudinal direction. The shaft hole 19a of the connection block 19 serves to guide the reciprocating linear motion of the delivery shaft 412. According to the exemplary embodiment of the present disclosure, a front end 415 of the delivery shaft 412 is inserted and disposed to be positioned inside more than the front end of the shaft hole 19a not to be exposed to the outside of the shaft hole 19a, but the front end 415 of the delivery shaft 412 may be disposed to be exposed close to the front end of the shaft hole 19a to be connectable to the driving force delivery unit 420.

Here, the delivery shaft 412 may be provided as a permanent magnet having predetermined magnetism. However, the entire delivery shaft 412 does not necessarily have to have the magnetism, and may also be provided such that only the front end of the delivery shaft 412, which is the connection portion with the connection bar which is one of the components of the driving force delivery unit 420 to be described later, has the magnetism. Further, the delivery shaft 412 does not have to be provided as the permanent magnet having the predetermined magnetism, and may be provided on the connection bar to be described later connected to the delivery shaft 412. At this time, the delivery shaft 412 may be made of a magnetic material such that the attractive force is applied against the connection bar. As the magnetic material, a ferromagnetic metal such as iron, cobalt, or nickel is preferably used, but the present disclosure is not limited thereto, and different kinds of materials may also be used as long as it is the magnetic material in which the attractive force is applied by the magnetism.

As illustrated in FIGS. 11 and 12, at least the delivery shaft 412 among the components of the driving unit 410 may be provided to be positioned on an emission light path unit 17a through which the emission light radiated by a light projector 700 passes and the tops of incident light path units 17b, 17c positioned on both left and right sides of the emission light path unit 17a and having the image of the oral cavity of the patient reflected and incident toward at least one camera and thus provided not to disturb the object to be measured. Both left and right sides of the emission light path unit 17a may be provided with the incident light path units 17b, 17c through which the image of the oral cavity of the patient is reflected and incident toward at least one camera.

As illustrated in FIGS. 12 and 13, the driving force delivery unit 420 is provided in the form of the connection bar, and connected to the front end of the delivery shaft 412 of the driving unit 410 to serve to deliver the linear driving force of the driving unit 410 to the optical element 60.

As described above, a rear end 421 of the connection bar, which is the driving force delivery unit 420, and the delivery shaft 412 may be magnetically coupled. More specifically, the rear end 421 of the connection bar may be formed with an insertion groove 421a into which a part of the front end 415 of the delivery shaft 412 is inserted, and the front end 415 of the delivery shaft 412 or the rear end 421 of the connection bar may be provided as the magnets to be magnetically coupled to each other, such that the front end 415 of the delivery shaft 412 may be magnetically coupled to each other by the operation of being inserted into the insertion groove 421a formed in the rear end 421 of the connection bar.

Further, the front end 415 of the delivery shaft 412 and the insertion groove 421a formed in the rear end 421 of the connection bar are formed to be engaged, such that the forcibly coupling, the hook coupling, or the like may be used, and the insertion groove may be formed in the front end 415 of the delivery shaft 412.

When the delivery shaft 412 is axially moved forward by a predetermined length in the longitudinal direction by the forward linear driving force delivered by the driving unit 410, the driving force delivery unit 420, which is the connection bar is linearly moved forward by a predetermined distance by the forward linear driving force according to the axial movement. Further, when the delivery shaft 412 is axially moved backward by a predetermined length in the longitudinal direction by the backward linear driving force delivered by the driving unit 410, in the portion magnetically coupled by the backward linear driving force according to the axial movement, a force of pulling the connection bar, which is the driving force delivery unit 420, backward in the longitudinal direction is generated as a kind of the attractive force, such that the connection bar, which is the driving force delivery unit 420, is linearly moved forward by a predetermined distance.

As illustrated in FIG. 13, a front end 422 of the connection bar as the driving force delivery unit 420 may be coupled by the hinge to the upper end of the optical element 60. When the linear driving force of the driving unit 410 is delivered to the optical element 60 via the driving force delivery unit 420 through the aforementioned driving mechanism, the optical element 60 may be tilted and rotated in the front and back direction around the predetermined axis to change the angles of the emission light emitted by the incident/emission light path unit 17 and the incident light incident by the incident/emission light path unit 17.

Figure 14:
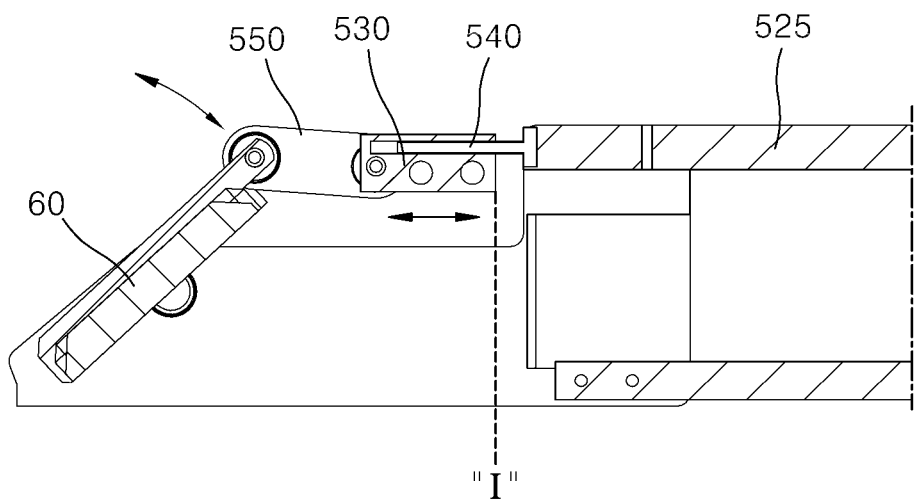
FIG. 14 is a partial cross-sectional diagram illustrating the operation state of a third light path change unit.
Figure 14:
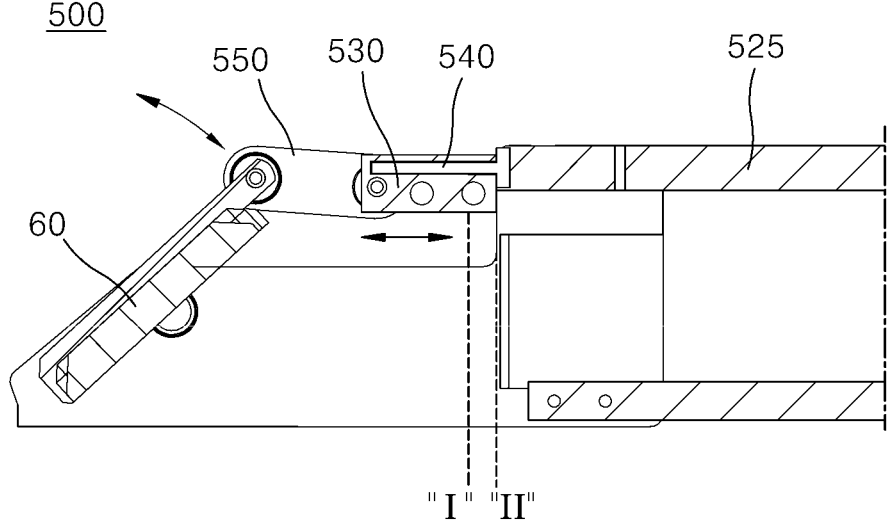

FIG. 14 is a partial cross-sectional diagram illustrating the operation state of a third light path change unit.

In the three-dimensional intraoral scanner according to the exemplary embodiment of the present disclosure, as illustrated in FIG. 14, a third light path change unit 500 may include a driving unit 530 provided on the top inside the tip case 14 to generate a linear driving force, and a hinge connection link 550 for hinge-connecting the rear end to the driving unit 530 and hinge-connecting the front end to the optical element 60 so as to receive the linear driving force generated by the driving unit 530 to tilt and rotate the optical element 60.

Unlike the aforementioned second light path change units 100, 400, the third light path change unit 500 has the driving unit 530 provided inside the front-end side of the tip case 14, and is configured to hinge-connect the driving unit 530 and the optical element 60, which are spaced apart from each other to be close to each other, through the hinge connection link 550.

Although not illustrated in the drawing, the third light path change unit 500 may be installed via an installation bracket provided inside the tip case 14.

The installation bracket may be formed to have the vertical cross section having an approximately '⊏' shape with the top opened, and formed with the aforementioned incident/emission light path unit 17 in the front and back direction between one sidewall and the other sidewall, thereby transmitting the emission light and the incident light.

Meanwhile, as illustrated in FIG. 14, the third light path change unit 500 may be provided to extend from the main body case 11 into the tip case 14, and may have a wiring casing body 525 for protecting a power source wire (not illustrated) for supplying a power source from a power supply unit (not illustrated) provided on the main body case 11 side to the driving unit 530, which is disposed in the front and back direction. At this time, the placement length of the wiring casing body 525 instead of the connection link 550 may be changed according to the position of the driving unit 530 provided inside the tip case 14. Here, the placement position of the driving unit 530 may be set between one end of the tip case 14 connected to the main body case 11 and the optical element 60.

The wiring casing body 525 is fixed to be horizontal to the top of the rear end of the installation bracket to serve to prevent the incident/emission light path unit 17 from being interfered by the internal power source wire, and to also serve as a medium for coupling the driving unit 530.

As illustrated in FIG. 14, the driving unit 530 may be provided as a solenoid motor linearly, reciprocally moved from the front end of the wiring casing body 525. The driving unit 530 provided as the solenoid motor may be linearly, reciprocally moved in the front and back direction along a fixed shaft 540.

Figure 18:
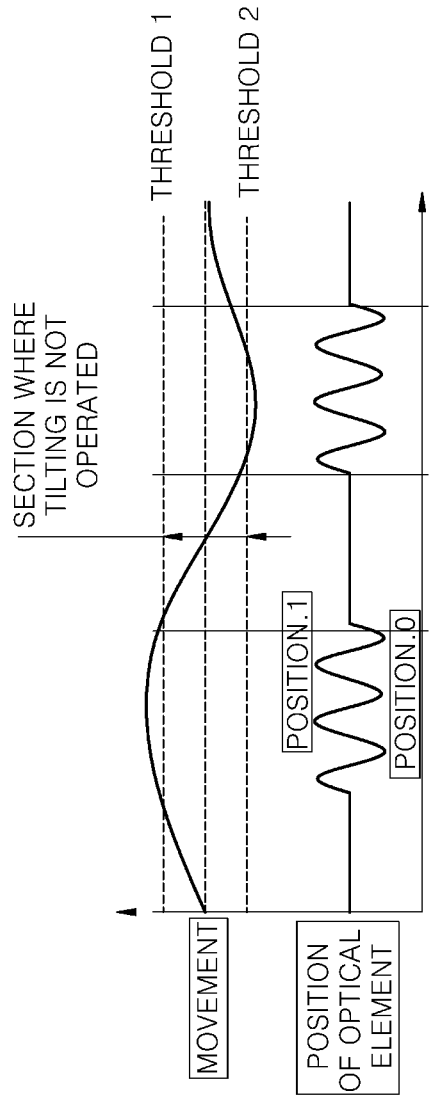
FIG. 18 is a control graph according to a third control embodiment of the three-dimensional intraoral scanner according to the exemplary embodiment of the present disclosure.

As illustrated in FIG. 18, the thus configured third light path change unit is electrically driven, such that when the driving unit 530 is moved forward by a predetermined distance from the front end of the wiring casing body 525, the upper end of the optical element 60 is tilted and rotated forward around a hinge shaft 60b while the hinge connection link 550 is moved forward (see FIG. 18A), and when the driving unit 530 is moved backward by a predetermined distance, the upper end of the optical element 60 is tilted and rotated backward around the hinge shaft 60b while the hinge connection link 550 is moved backward (see FIG. 18B). That is, the driving unit 530 tilts and rotates the optical element 60 several times while reciprocally moving in the section between approximately "I" and "II" several times from the front end of the wiring casing body 525.

In the three-dimensional intraoral scanner 1 according to the exemplary embodiment of the present disclosure, the light path change units 80, 100, 400 may allow the optical element 60 to perform the rotation motion to adjust the introduction path (incident path) of the light, and also allow the optical element 60 itself to perform the linear motion to adjust the introduction path (incident path) of the light.

Further, the three-dimensional intraoral scanner according to the exemplary embodiment of the present disclosure may further include a control unit (not illustrated) for interlocking and adjusting the light path change units 80, 100, 400 and the aforementioned image acquisition unit 20.

The control unit may include one of an interlocking adjustment unit 15, an angle adjustment unit, and a movement amount control unit. Here, the control unit may operate and control the driving units 90, 110, 410 based on control signals delivered by the interlocking adjustment unit 15, the angle adjustment unit, and the movement amount control unit. The driving units 90, 110, 410 operated by the control unit delivers a predetermined driving force to the driving force delivery units 97, 120, 420, such that the optical element 60 performs the rotation motion or the linear motion.

Furthermore, the control unit may further include an adjustment amount range control unit (not illustrated) for determining and controlling the adjustment angle and an amount of movement of the angle adjustment unit for each device (or each product to which the exemplary embodiment of the present disclosure is specifically applied).

When the control unit 15 receives the control signal from the interlocking adjustment unit 15 or the angle adjustment unit, the adjustment amount range control unit may allow the light path change units 80, 100, 400 to consecutively adjust the optical element 60 to be changed by a plurality of preset light path changing amounts.

Further, when the control unit receives the control signal from the movement amount control unit, the adjustment amount range control unit may allow the light path change units 80, 100, 400 to adjust the optical element 60 to be linearly moved by a preset position.

Here, the control unit does not necessarily have to be provided inside the main body case 11 or the tip case 14 of the three-dimensional intraoral scanner according to the present disclosure, and although not illustrated in the drawing, may also be provided in a control PC connected to the three-dimensional intraoral scanner to be data communicable with each other, and in this case, the control PC may also be provided to input a value for changing the light path through an input means (e.g., a keyboard) of the control PC provided to take over the role of the interlocking adjustment unit 15, the angle adjustment unit, or the movement amount control unit while being responsible for the aforementioned function of the control unit.

Meanwhile, immediately after the controls of the light path change units 80, 100, 400 are completed by the control unit, or during the control process, the interlocking control of the image acquisition unit 20 may also be performed to obtain the desired three-dimensional image data within the oral cavity.

More specifically, by the control unit, when a target angle (or a setting angle) of the optical element 60 is input by the operation of applying a predetermined control signal to the light path change units 80, 100, 400, the angle of the optical element 60 may be adjusted by the operation of controlling the operation times of the light path change units 80, 100, 400 based on the linear motion amount of a predetermined point of the optical element 60.

The predetermined point refers to any position (point) of the surface of the optical element 60, which is somewhat spaced apart from the predetermined axis, and the linear motion amount may be defined as the length of the arc using the predetermined axis as the center of the circle.

Here, since driving speeds of the driving units 90 of the light path change units 80, 100, 400 for driving the optical element 60 are already known, if a predetermined control signal is applied by the control unit and the target angle (the setting angle) of the optical element 60 is input, the control unit may control the operation time of the driving unit 90 to adjust a final angle of the optical element 60.

Further, if the driving unit 90 is provided as the piezo, the angle may be adjusted by a predetermined angle determined as a bending angle of the piezo rotating the optical element 60 by applying the predetermined control signal by the control unit.

Figure 15:
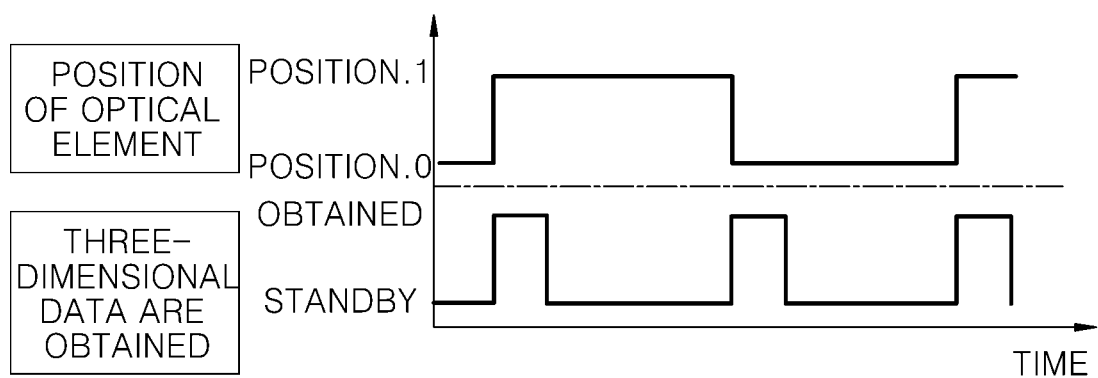
FIG. 15 is a control graph illustrating a process of obtaining the three-dimensional data according to the position of the optical element among the components of the three-dimensional intraoral scanner according to the exemplary embodiment of the present disclosure.

FIG. 15 is a control graph illustrating a process of obtaining the three-dimensional data according to the position of the optical element among the components of the three-dimensional intraoral scanner according to the exemplary embodiment of the present disclosure.

A process of obtaining the three-dimensional data using the three-dimensional intraoral scanner according to the exemplary embodiment of the present disclosure will be briefly described with reference to FIG. 15 as follows. Hereinafter, for the convenience of understanding, a reference tilting point of the optical element 60 is indicated by a position.0, and the maximum tilting point is indicated by a position.1.

That is, referring to FIG. 15, to scan the oral cavity during one cycle defined from the position.0 to the position.1, the interlocking adjustment unit 15 may completely adjust the angle of the optical element 60 and then operate the image acquisition unit 20 in the standby state to obtain the three-dimensional data. Of course, it is natural that the angle of the optical element 60 is adjusted from the position.1 to the position.0 and then the three-dimensional data may be obtained. That is, the three-dimensional data may be obtained at the initial position (position.0) of the optical element 60, the three-dimensional data may be obtained again at the position at which the angle is completely adjusted (position.1), and the three-dimensional data may be obtained while restoring the optical element 60 back to the original position.

Figure 16:
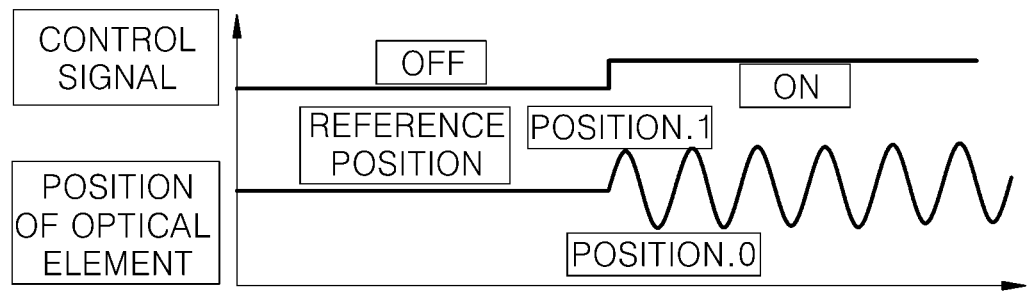
FIG. 16 is a control graph according to a first control embodiment of the three-dimensional intraoral scanner according to the exemplary embodiment of the present disclosure.
Figure 17:
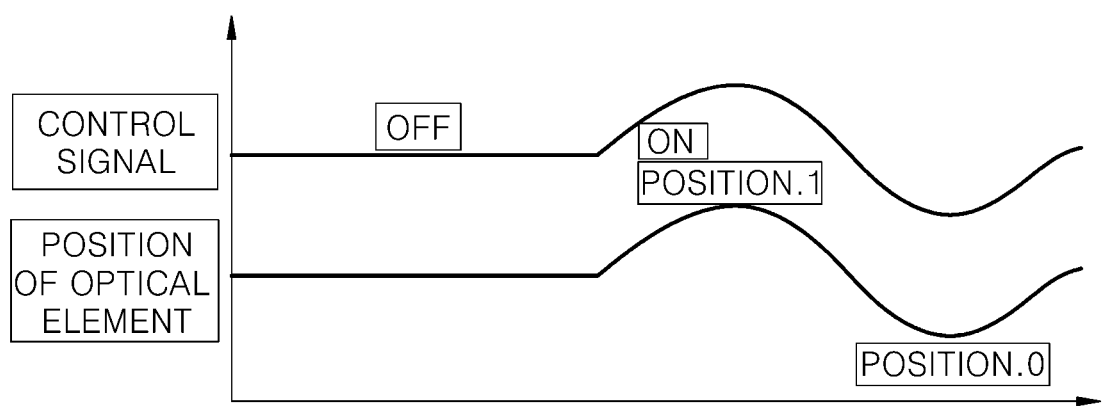
FIG. 17 is a control graph according to a second control embodiment of the three-dimensional intraoral scanner according to the exemplary embodiment of the present disclosure.

FIG. 16 is a control graph according to a first control embodiment of the three-dimensional intraoral scanner according to the exemplary embodiment of the present disclosure, FIG. 17 is a control graph according to a second control embodiment of the three-dimensional intraoral scanner according to the exemplary embodiment of the present disclosure, and FIG. 18 is a control graph according to a third control embodiment of the three-dimensional intraoral scanner according to the exemplary embodiment of the present disclosure.

Referring to FIG. 16, an operator confirms in real time whether the image is obtained by a display unit (not illustrated) for visually displaying the completed state of the three-dimensional data obtained in conjunction with the three-dimensional intraoral scanner according to the present disclosure, and operates the interlocking adjustment unit 15 to tilt and control the optical element 60, if it is determined that the image data is not sufficiently obtained in some measurement regions such as the throat side of the patient or a narrow space between the teeth and the lips of the patient.

As described above, when the control signal is turned on by the interlocking adjustment unit 15, the first light path change unit to the third light path change unit 80, 100, 400, 500 may automatically tilt and rotate the optical element 60 several times between the position.0 and the position.1 based on the control signal to sufficiently obtain the three-dimensional image data.

Referring to FIG. 17, likewise, the operator confirms in real time whether the image is obtained by the display unit and then tilts and rotates the optical element 60 by the desired angle to additionally obtain the image data of the portion where the three-dimensional image data is not obtained using the angle adjustment unit, if it is determined that the image data is not sufficiently obtained.

As described above, when the control signal interlocking with the adjustment of the angle adjustment unit is turned on, the first light path change unit to the third light path change unit 80, 100, 400, 500 may tilt and rotate the optical element 60 between the position.0 and the position.1 based on the control signal to obtain the additional image data.

Meanwhile, as a case of automatically obtaining the three-dimensional data according to the position or inclination of the main body case 11 without providing the interlocking adjustment unit and the angle adjustment unit, referring to FIG. 18, likewise, the operator may confirm in real time whether the image is obtained by the display unit and then move the main body case 11 vertically and move the main body case 11 to exceed a preset upward threshold 1 and a preset downward threshold 2, if it is determined that the image data is not sufficiently obtained, thereby operating the optical element 60 to be automatically tilted and rotated several times in the portion of exceeding each threshold. Further, if the movement of the main body case 11 reaches the threshold 1, the optical element 60 may be tilted and rotated in the direction of the position.1, or conversely, if the movement of the main body case 11 reaches the threshold 2, the optical element 60 may be tilted and rotated in the direction of the position.0, thereby sufficiently obtaining the image data between the threshold 1 and the threshold 2. The tilting rotation of the optical element 60 is the case where the movement of the main body case 11 within each threshold is sensed, and may be stopped by an OFF signal perceived.

Here, the main body case 11 may be provided such that the movement of the position, the inclination, or the like of the main body case 11 is sensed by an acceleration sensor (not illustrated) or a gyro sensor (not illustrated) provided in the main body case 11.

FIG. 19 is a graph illustrating a process of automatically obtaining the three-dimensional data in all sections using a three-dimensional intraoral scanner according to another exemplary embodiment of the present disclosure.

Although not illustrated in the drawing, a three-dimensional intraoral scanner according to another exemplary embodiment of the present disclosure may be provided to automatically calculate the image information (e.g., an amount of light, focus, hole information, and the like) incident through the opening 16, when the operator turns on the three-dimensional intraoral scanner using the interlocking adjustment unit 15.

As illustrated in FIG. 19, the thus provided three-dimensional intraoral scanner according to another exemplary embodiment of the present disclosure stores image information of an image incident through the opening 16, determines that the corresponding image information is insufficient when at least one information among the image information is calculated by the aforementioned operation unit and the calculated information does not satisfy a setting value, and turns on the first light path change unit to the third light path change unit 80, 100, 400, 500. Then, the insufficient image data may be additionally obtained while the optical element 60 is automatically tilted and rotated several times between the position.0 and the position.1 or tilted and rotated at one of the position.0 and the position.1, and the first light path change unit to the third light path change unit 80, 100, 400, 500 are turned off if the image information satisfies the setting value through the additional obtained image data.

As described above, the three-dimensional intraoral scanners 1 according to the exemplary embodiment and another exemplary embodiment of the present disclosure may be particularly provided with the optical element 60 to be rotatable using the first light path change unit to the third light path change unit 80, 100, 400, 500 to change the incident angle of the incident light incident through the opening 16, thereby very easily obtaining the three-dimensional data for the teeth close to the throat side at which it is actually difficult to obtain the three-dimensional data inside the oral cavity of the patient or the teeth positioned in the narrow space between the teeth and the lips.

The aforementioned description is merely to exemplarily describe the technical spirit of the present disclosure, and various modifications and changes will be possible by those skilled in the art to which the present disclosure pertains without departing from the essential characteristics of the present disclosure.

Therefore, the exemplary embodiments disclosed in the present disclosure do not limit the technical spirit of the present disclosure but describe it, and the scope of the technical spirit of the present disclosure is not limited to the exemplary embodiments. The protective scope of the present disclosure should be interpreted by the appended claims, and all technical spirit within the scope equivalent thereto should be interpreted as being included in the scope of the present disclosure.

INDUSTRIAL APPLICABILITY

The present disclosure provides the three-dimensional intraoral scanner, which may actively rotate the optical element to adjust the angle of the optical element with respect to the portion having the spatial constraint when the oral cavity of the patient is measured, thereby obtaining the three-dimensional data of the specific portion even without moving the entire case.

The invention claimed is:

1. A three-dimensional intraoral scanner comprising:
a case drawn in and out of the oral cavity, and formed with an opening opened such that the appearance inside the oral cavity is introduced into the case in the form of light through one end of the case;
at least one camera disposed inside the case, and disposed to allow the light introduced through the opening of the case to pass;
a light projector disposed on one side of the at least one camera to radiate light through the opening;
an optical element configured to be tilted and rotated while reflecting or refracting the path of the light of the at least one camera and the light projector inside the case;
a light path change circuitry for moving the optical element to be adjustable; and
an interlocking adjustment circuitry for interlocking and adjusting the light path change circuitry and the at least one camera.

2. The three-dimensional intraoral scanner of claim 1, wherein the light path change circuitry comprises:
a driver which is electrically driven; and
a driving force delivery circuitry for delivering the driving force generated by the driver to the optical element.

3. The three-dimensional intraoral scanner of claim 2, wherein the driver comprises: any one of a motor, a piezo, a MEMS, and a solenoid.

4. The three-dimensional intraoral scanner of claim 3, wherein the piezo comprises: a bending circuitry connected to the optical element and provided to be bent by providing a voltage.

5. The three-dimensional intraoral scanner of claim 2, wherein the case comprises: a main body case provided with an image acquisition unit and a tip case provided with the optical element, and
wherein the driver is provided inside the main body case.

6. The three-dimensional intraoral scanner of claim 2, wherein the driver and the driving force delivery circuitry are connected in a detachably coupling method.

7. The three-dimensional intraoral scanner of claim 2, wherein the driver and the driving force delivery circuitry are connected in a magnetically coupling method.

8. The three-dimensional intraoral scanner of claim 2, wherein the driver and the driving force delivery circuitry are connected in a fixedly coupling method.

9. The three-dimensional intraoral scanner of claim 1, wherein the light path change circuitry comprises:
a driver for generating a linear driving force for tilting and rotating the optical element; and
a driving force delivery circuitry for delivering the linear driving force generated by the driver to the optical element, and
wherein the driving force delivery circuitry is provided in the form of the connection bar connecting the driver to the optical element.

10. The three-dimensional intraoral scanner of claim 1, wherein the light path change circuitry comprises:
a driver for generating a linear driving force for tilting and rotating the optical element; and
a driving force delivery circuitry for delivering the linear driving force generated by the driver to the optical element, and
wherein the driving force delivery circuitry is provided in the form of the hinge connection link connecting the driver to the optical element.

11. The three-dimensional intraoral scanner of claim 1, wherein the light path change circuitry allows the optical element to perform the rotation motion to adjust the introduction path of the light.

12. The three-dimensional intraoral scanner of claim 1, wherein the light path change circuitry allows the optical element to perform the linear motion to adjust the introduction path of the light.

13. The three-dimensional intraoral scanner of claim 12, further comprising: a movement amount controller for controlling an amount of movement upon the linear motion of the optical element.

14. The three-dimensional intraoral scanner of claim 1, further comprising: an angle adjustment circuitry for controlling an adjustment angle upon the rotation motion of the optical element.

15. The three-dimensional intraoral scanner of claim 14, further comprising: an adjustment amount range controller for determining and controlling the range of the adjustment angle or the amount of movement for each device.

16. The three-dimensional intraoral scanner of claim 1, wherein the interlocking adjustment circuitry allows the light path change circuitry to consecutively adjust the optical element to be changed by a plurality of preset light path change amounts.

17. A three-dimensional intraoral scanner comprising: a case drawn in and out of the oral cavity, and formed with an opening opened such that the appearance inside the oral cavity is introduced into the case in the form of light through one end of the case;
at least one camera disposed inside the case, and disposed to allow the light introduced through the opening of the case to pass;
a light projector disposed on one side of the at least one camera to radiate light through the opening;
an optical element provided to be tilted and rotated while reflecting or refracting the path of the light of the at least one camera and the light projector inside the case;

a light path change circuitry for moving the optical element to be adjustable; and an interlocking adjustment circuitry for controlling to interlock and adjust the operation of the light path change circuitry and the at least one camera in order to move the optical element to be adjustable, wherein the interlocking adjustment circuitry controls to tilt the optical element, if it is determined that the image data obtained by the introduction of the light are insufficient.

* * * * *